United States Patent [19]

Haas

[11] Patent Number: 4,859,704

[45] Date of Patent: Aug. 22, 1989

[54] WATER SOLUBLE IBUPROFEN COMPOSITIONS AND METHODS OF MAKING THEM

[75] Inventor: Ronald T. Haas, West Windsor Township, Mercer County, N.J.

[73] Assignee: Oratech Pharmaceutical Development Corporation, Princeton, N.J.

[21] Appl. No.: 173,299

[22] Filed: Mar. 25, 1988

Related U.S. Application Data

[63] Continuation-in-part of Ser. No. 110,184, Oct. 15, 1987.

[51] Int. Cl.$^4$ ............................................. A61K 31/19
[52] U.S. Cl. .................................................... 514/557
[58] Field of Search ............... 424/485, 486, 484, 456, 424/488; 514/557

[56] References Cited

U.S. PATENT DOCUMENTS

| | | |
|---|---|---|
| 3,041,239 | 6/1962 | Nashed . |
| 3,228,831 | 1/1966 | Nicholson et al. . |
| 3,385,886 | 5/1968 | Nicholson et al. . |
| 3,733,410 | 5/1973 | Asche . |
| 3,903,297 | 9/1975 | Robert . |
| 3,911,137 | 10/1975 | Miki et al. . |
| 3,927,205 | 12/1975 | Ohno et al. . |
| 4,031,243 | 6/1977 | Aparicio et al. . |
| 4,145,440 | 3/1979 | Fitch et al. . |
| 4,282,252 | 8/1981 | Lefer . |
| 4,344,929 | 8/1982 | Bonsen et al. . |
| 4,346,108 | 8/1982 | Singer . |
| 4,361,580 | 11/1982 | Peck et al. . |
| 4,389,393 | 6/1983 | Schor et al. . |
| 4,404,210 | 9/1983 | Schmidt . |
| 4,439,450 | 3/1984 | Coleman . |
| 4,447,443 | 5/1984 | Goldenberg . |
| 4,447,451 | 5/1984 | Mueller . |
| 4,536,595 | 8/1985 | Gardano et al. . |
| 4,545,992 | 10/1985 | Kamashita . |
| 4,552,899 | 11/1985 | Sunshine et al. . |
| 4,555,524 | 11/1985 | Gruber et al. . |
| 4,558,051 | 12/1985 | Sunshine et al. . |
| 4,569,937 | 2/1986 | Baker et al. . |
| 4,571,400 | 2/1986 | Arnold . |
| 4,587,252 | 5/1986 | Arnold . |
| 4,599,359 | 7/1986 | Cooper . |
| 4,609,675 | 9/1986 | Franz . |
| 4,619,934 | 10/1986 | Sunshine et al. . |
| 4,681,897 | 7/1987 | Brand . |
| 4,687,662 | 8/1987 | Schobel . |
| 4,689,218 | 8/1987 | Gazzaniga et al. . |
| 4,690,823 | 9/1987 | Lohner et al. . |
| 4,713,249 | 12/1987 | Schroder . |
| 4,717,713 | 1/1988 | Zatz et al. . |
| 4,726,966 | 2/1988 | Kawashima et al. . |
| 4,788,220 | 11/1988 | Mody et al. .......................... 514/557 |

FOREIGN PATENT DOCUMENTS

| | | |
|---|---|---|
| 1197254 | 11/1986 | Canada . |
| 0068838 | 1/1983 | European Pat. Off. . |
| 0137668 | 4/1985 | European Pat. Off. . |
| 2000322 | 7/1970 | Fed. Rep. of Germany . |
| 2400363 | 3/1979 | France . |
| 867803 | 5/1961 | United Kingdom . |
| 2079600 | 1/1982 | United Kingdom . |

OTHER PUBLICATIONS

Moore et al., "Postextraction Pain Relief in Children: A Clinical Trial of Liquid Analgesics", *International Journal of Clinical Pharmacology, Therapy and Toxicology*, vol. 23, No. 11-1985, pp. 573-577.

Morrison et al., *Organic Chemistry*, Third Edition, 1973, pp. 579-584.

Norman et al., "A Double-Blind Comparison of a New Ibuprofen-Codeine Phosphate Combination, Codeine Phosphate, and Placebo in the Relief of Postepisiotomy Pain", *Clinical Therapeutics*, vol. 7, No. 5, 1985, pp. 549-554.

Martindale, *The Extra Pharmacopoeia*, 27th Edition, 1977, pp. 192, 193, 915-917, 931, 932, 1265-1267, 1442-1446.

Adams et al., "The Pharmacological Properties of Ibuprofen, An Anti-Inflammatory, Analgesic and Anti-Pyretic Agent", *Arch. int. Pharmacodyn.*, 1969, vol. 178, No. 1, pp. 115-129.

Glenn et al., "In Vitro Effects of Non-Steroidal Anti--Inflammatory Drugs (NAIFD)", *Proc. Soc. Erp Med.*, vol. 130, 1969, pp. 1327-1332.

Huskisson et al., "Ibuprofen, A Review", *Practitioner*, vol. 207, 1971, pp. 639-643.

Brooks et al., "Tolerance and Pharmacology of Ibuprofen", *Current Therapeutic Research*, vol. 15, No 4, Apr. 1973, pp. 180-190.

"Summary Basis of Approval of Nuprin", 1984, NDA 19-012, Section IV, p. 2 and Section V, pp. 3-27.

Motrin, Physician's Desk Reference, 41st Edition, 1987, pp. 2058-2060.

Sheth et al., "Measurement of Antipyretic Activity of Ibuprofen and Paracetamol in Children", *J. Clin. Pharmacol.*, vol. 20, 1980, pp. 672-675.

Gaitonde et al., "Antipyretic Activity of Ibuprofen (Brufen)", *J. Assoc. Physicians India*, vol. 21, 1973, pp. 579-584.

Simila et al., "Oral Antipyretic Therapy, Evaluation of Ibuprofen", *Scand J Rheumatology*, vol. 5, 1976, pp. 81-83.

Phadke, et al., "Ibuprofen in Children with Infective Disorders-Antipyretic Efficacy", *Br J Clin Pract*, Nov.-Dec. 1985, pp. 437-440.

Amdekar et al., "Antipyretic Activity of Ibuprofen and (List continued on next page.)

Primary Examiner—Nancy A. B. Swisher
Attorney, Agent, or Firm—Indyk, Pojunas & Brady

[57] ABSTRACT

A novel water soluble alkali metal salt of ibuprofen is prepared by reacting ibuprofen and an alkali metal bicarbonate in a aqueous medium. The salt is useful in treating pain, inflammation, and fever in mammals. It permits the preparation of a number of novel formulations which result in pharmaceutically and commercially acceptable dosage forms.

26 Claims, No Drawings

OTHER PUBLICATIONS

Paracetamol in Children with Pyrexia", *Brit J Clin Pract*, Apr. 1985, pp. 140–143.

Kandoth, et al., "Comparative Evaluation of Antipyretic Activity of Ibuprofen and Aspirin in Children with Pyrexia of Varied Aetiology", *J. Int. Med. Res.*, vol. 12, 1984, pp. 292–297.

Kotob, "A Comparative Study of Two Dosage Levels of Ibuprofen Syrup in Children with Pyrexia", *J. Int. Med. Res.*, vol. 13, 1985, pp. 122–126.

Adams et al., "Some Biological Properties of 2-(-4-Isobutylphenyl)-propionic Acid", *J. Pharm. Sci.*, vol. 56, 1967, p. 1686.

Davis, "Drug Evaluation Data, Ibuprofen", *Drug Intelligence and Clinical Pharamcy*, vol. 9, 1979, pp. 501–503.

Adams et al., "Ibuprofen and Flurbiprofen", *Clinics in Rheumatic Diseases*, vol. 5, No. 2, Aug. 1979, pp. 359–379.

Greenblatt et al., "Absorption and Disposition of Ibuprofen in the Elderly", *Arthritis and Rheumatism*, vol. 27, No. 9, Sep. 1984, pp. 1066–1069.

Whitehall Company Product Monograph, Advil, 1984, p. 43.

Blechman et al., "Ibuprofen or Aspirin in Rheumatoid Arthritis Therapy", *Journal of the American Medical Association*, vol. 233, pp. 336–339.

Dornan et al., "Comparison of Ibuprofen and Acetylsalicylic Acid in the Treatment of Rheumatoid Arthritis", *CMA Journal*, vol. 110, Jun. 22, 1974, pp. 1370–1372.

Royer et al., "A Six-Month Double-Blind Trial of Ibuprofen and Indomethacin in Osteoarthritis", *Current Therapeutic Research*, vol. 17, No. 2, Mar. 1975, pp. 234–248.

Muckle, "Comparative Study of Ibuprofen and Aspirin in Soft-Tissue Injuries", *Rheumatol. and Rehab.*, vol. 13, 1974, pp. 141–147.

Abstract of Vecchio, et al., "Efficacy of Ibuprofen in Muscle Contraction Headache", *Clinical Pharmacology & Therapeutics*, vol. 33, No. 2, 1983, p. 199.

Shapiro et al., "The Effect of Ibuprofen in the Treatment of Dysmenorrhea", *Curr. Ther. Res.*, vol. 30, pp. 327–333.

Cooper et al., "Comparative Analgesic Potency of Aspirin and Ibuprofen", *J Oral Surgery*, vol. 35, Nov. 1977, pp. 898–903.

Bloomfield et al., "Comparative Efficacy of Ibuprofen and Aspirin in Episiotomy Pain", *Clin. Pharmacol. Ther.*, vol. 15, 1974, pp. 565–570.

Perry et al., "Ibuprofen Overdose: The First Two Years of Over-The-Counter Sales", *Human Toxocol.*, vol. 6, 1987, pp. 173–178.

Hall et al., "Ibuprofen Overdose: 126 Cases", *Annals. of Emergency Medicine*, vol. 15, Nov. 1986, pp. 1308–1313.

Bibliography (1966 to Apr. 1988), Obtained from a Search of the Medli Computer Data Base Calling for all Documents with the Word "Ibuprofen" in the Titles.

Computer Printouts Resulting from Searches of the Following Computer Data Bases for Documents Containing the Words "Ibuprofen", and any of Child, Pediatric, or Infant: Dialog, Medline, International Pharmaceutical Abstracts, Pharmaceutical News Index, and Clinical Abstracts.

WATER SOLUBLE IBUPROFEN COMPOSITIONS AND METHODS OF MAKING THEM

CROSS REFERENCE TO RELATED PATENT APPLICATION

This application is a continuation-in-part of Application Ser. No. 110,184 of Ronald T. Haas, filed in the Patent and Trademark Office on Oct. 15, 1987, entitled LIQUID IBUPROFEN COMPOSITIONS AND METHODS OF MAKING THEM, the entire disclosure of which is incorporated herein by reference.

FIELD OF THE INVENTION

The invention of this application relates to water soluble ibuprofen compositions. More particularly, the invention relates to alkali metal salts of ibuprofen, methods of preparing alkali metal salts of ibuprofen, and formulations and dosage forms of alkali metal salts of ibuprofen. These compositions are useful in treating pain, inflammation and fever. They may be used in conjunction or in combination with other medications, such as cough medications, cold medications, antihistamines, decongestants, or narcotics, or combinations of two or more of these medications. They may be used in any dosage form, such as tablets, capsules, liquids, or parenterals.

BACKGROUND OF THE INVENTION

Ibuprofen (p-isobutylhydratropic acid) is a nonsteroidal composition that has long been recognized as being useful in the treatment of pain, inflammation, and fever. More particularly, ibuprofen has been found in clinical studies to be very effective in the treatment of the signs and symptoms of rheumatoid arthritis and osteoarthritis, the relief of mild to moderate pain, and the treatment of primary dysmenorrhea, among other things. Ibuprofen is at least as effective as other available high potency compounds, such as indomethacin and phenylbutazone, but without their attendant side effects, such as increased toxicity. Also, ibuprofen is obtainable over the counter in certain dosages, whereas other high potency compounds are not.

There has been a long felt need for an analgesic composition which is safe, effective, and capable of being formed into a pharmaceutically elegant product. Two compositions tried in the past are aspirin and acetaminophen. There are several disadvantages in using these compositions as compared with using ibuprofen. First, the analgesia produced by a given amount of aspirin or acetaminophen is less than that produced by the same amount of ibuprofen. Second, acetaminophen compositions lack anti-inflammatory activity. Third, aspirin compositions produce significantly more gastrointestinal distress in some patients. Fourth, aspirin has been reported linked to Reye's syndrome in children. Fifth, acetaminophen has been reported to cause liver failure in some patients and has been more recently been questioned about its possible link to renal disorders.

Although ibuprofen is a significantly better analgesic than aspirin or acetaminophen, there are notable problems in preparing satisfactory dosage forms of ibuprofen. These problems include the facts that ibuprofen is insoluble in water, has a very bitter taste, and is unstable in aqueous media.

Applicant has essentially solved all of these problems in one stroke by preparing and using alkali metal salts of ibuprofen. These salts are easily dissolved in water, they permit preparation of pharmaceutical compositions which are virtually lacking in the unpleasant taste sensations of ibuprofen, and they are stable in aqueous media. They are more easily taken up by the body and they involve less gastrointestinal distress than conventional ibuprofen compositions.

There has been some theoretical speculation about the possibility of preparing alkali metal salts of ibuprofen, but to Applicant's knowledge, there has never been anything indicating that such salt have ever been put in the hands of the public. To Applicant's knowledge, there has never been an alkali metal salt of ibuprofen actually prepared by any process, nor has there been any publication of any information sufficient to enable a person skilled in the art to make and use an alkali metal salt of ibuprofen or appreciate its advantageous properties.

For example, Gardano et al. U.S. Pat. No. 4,536,595 describes the preparation of an alpha-aryl-propionic acid from a corresponding organic halide and carbon monoxide in the presence of a catalytic system based on cobalt carbonyl complexes and alkaline metal hydroxides. The patent refers to preparation of alkaline salts of alpha-aryl-propionic acids, but does not describe the preparation of those salts beyond the description of a process involving a liquid composition which might contain the ions that if bonded together theoretically would be an alkali metal salt of an alpha-aryl-propionic acid. The patent does not describe a process which produces an actual salt, even though it says it does. In all instances, the only thing produced by the processes of the patent is the alpha-aryl-propionic acid and not a salt. There thus is no enabling disclosure of such a salt.

Canadian Patent No. 1 197 254 describes a process which is similar to that of the Gardano et al. patent described above. Likewise, there is no description of how alkaline salts of alpha-aryl-propionic acids are to patent be made and thus this patent is like the Gardano et al. patent in failing to enable one skilled in the art to achieve such alkaline salts.

U.S. Pat. No. 3,385,886 describes phenyl propionic acids. It says that the salts of the acids can be made by reacting the acids with organic or inorganic bases. There is no enabling disclosure of how to prepare alkali metal salts of ibuprofen.

Another patent which can only be said to identify an alkali metal salt of ibuprofen as a theoretical possibility and not to describe it in an enabling manner is Schmidt U.S. Pat. No. 4,404,210, which mentions aluminum, calcium, potassium, and sodium salts of ibuprofen.

This application is the first enabling disclosure of alkali metal salts of ibuprofen and a process of making them It is also the first instance of identifying the advantageous properties of such salts of ibuprofen and its uses in alleviating pain, inflammation, and fever. It likewise is the first instance of teaching how the salts may be put into pharmaceutically acceptable and elegant dosage forms.

SUMMARY OF THE INVENTION

It is an object of the invention to provide a novel ibuprofen composition, particularly the alkali metal salts of ibuprofen.

It is also an object of the invention to provide a method of making those novel ibuprofen compositions, particularly a method which is simple and economical and uses readily available materials.

It is a further object of the invention to provide an ibuprofen composition which avoids the problems of prior ibuprofen compositions, while at the same time preserve the benefits of those ibuprofen compositions.

It is an additional object of the invention of this application to make novel formulations resulting in pharmaceutically elegant and commercially viable solid and liquid dosage forms of ibuprofen compositions.

Other objects and advantages of the invention are either described specifically elsewhere in this application or are apparent from that description.

The invention involves an alkali metal salt of ibuprofen. The salt may be prepared by dissolving a predetermined amount of an alkali metal bicarbonate in an aqueous medium and then dissolving a predetermined amount of ibuprofen in the aqueous medium containing the bicarbonate composition. The solid, crystalline alkali metal salt may be extracted from the aqueous medium and may be administered to mammals in any solid or liquid dosage form to treat pain, inflammation and fever.

DETAILED DESCRIPTION OF THE INVENTION

Alkali metal salts of ibuprofen in accordance with the invention of this application may be prepared by dissolving a predetermined amount of an alkali metal bicarbonate composition in a predetermined amount of water. The nature of the bicarbonate composition determines the resulting salt. One example of bicarbonate composition which may be used in the invention is sodium bicarbonate, which produces a sodium salt of ibuprofen. In a preferred example of the invention, potassium bicarbonate is used, which results in a potassium salt of ibuprofen.

After the bicarbonate composition has been dissolved in the water, a predetermined amount of ibuprofen is dissolved in the water. The amount of bicarbonate composition used should be at least an amount such that the number of moles of bicarbonate composition equals the number of moles of ibuprofen used. It may be desirable to use a greater number of moles of bicarbonate composition than the number of moles of ibuprofen to promote the complete and rapid dissolution of the ibuprofen into the aqueous medium and the efficient conversion of ibuprofen into the ions which will later form the alkali metal salt. In this regard, when the bicarbonate composition and ibuprofen are dissolved in the aqueous medium, a reaction takes place which results in an aqueous solution containing ions capable of bonding together in a solid crystalline salt of ibuprofen as follows:

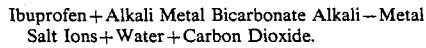
Ibuprofen+Alkali Metal Bicarbonate Alkali—Metal Salt Ions+Water+Carbon Dioxide.

It is advantageous to stir the aqueous medium as the bicarbonate composition and ibuprofen are being dissolved and to dissolve those materials while keeping the aqueous medium at an elevated temperature which will not adversely affect the materials being dissolved, for example, at an elevated temperature no greater than about 55 to 65 degrees Centigrade.

As the ibuprofen is added to the aqueous medium containing the bicarbonate composition, a foaming action occurs, as would be expected from the production of carbon dioxide in the reaction identified above. This foam should be allowed to subside and then a clear aqueous solution of ibuprofen salt will result. At this point, the solid, crystalline alkali metal salt may be extracted in any conventional manner. For example, the water in the solution may be evaporated, a process which may be hastened by raising the temperature and exposing the solution to a vacuum. Another way to extract the ibuprofen salt is by a freeze drying process.

The solid crystalline salt may then be milled into a powder and used to prepare any dosage form for administration to a mammal for the relief of pain, inflammation, and fever. For example, the salt may be formed into a solid dosage in the form of a tablet, a capsule, or suppository. It may also be redissolved in an aqueous medium to form a liquid dose such as a solution or suspension which may be administered orally or parenterally.

An alkali metal ibuprofen salt in accordance with the invention has the advantages that it is water soluble, which means that clear solutions may be prepared and that the analgesic is readily taken up by the body so that its effects may be obtained rapidly and effectively. Also, it is believed that less gastrointestinal distress results from the use of the alkali metal salts of ibuprofen rather than ibuprofen itself. Specifically, an alkali metal salt in accordance with the invention permits the preparation of compositions that have close to neutral pH or do not in any way interfere with the natural pH balance in the body, especially the pH in the stomach and the rest of the gastrointestinal tract. It is believed that compositions having pH's close to neutral in the manner of this composition or which do not upset or influence the body's natural pH balance in any significant way are instrumental in reducing the gastrointestinal distress that was experienced when prior acidic compositions such as aspirin or ibuprofen were administered.

EXAMPLE 1

A particularly advantageous solid dose tablet composition containing 400 mg. of the potassium salt of ibuprofen per tablet may be prepared as follows with the ingredients listed below:

| Ingredient | Quantity |
| --- | --- |
| Part I | |
| Potassium Ibuprofen Salt (Active Ingredient) | 40.0 kg. |
| Part II | |
| Starch NF (Corn Starch) (Binder) | 2.0 kg. |
| Gelatin USP (Binder) | 1.0 kg. |
| Purified Water USP (Solvent) | 15.0 L. |
| Part III | |
| Lactose USP Spray Process (Filler, Binder) | 9.0 kg. |
| Starch NF (Corn Starch) (Binder) | 5.8 kg. |
| Sodium Starch Glycolate NF (Explotab) (Binder) | 1.5 kg. |
| Cabosil M-5 Powder (Colloidal Silicon Dioxide NF) (Lubricant) | 300 g. |
| Part IV | |
| Magnesium Stearate NF Imp. Powder (Lubricant) | 400 g. |

The following dry granulation equipment may be used in this process:
1. A Marion Mixer G-5;
2. A Fitzmill;
3. A Drying Oven;
4. An Oscillator; and
5. A Number of Screens Comprising:
   (a) #3-P and #4-P mesh screens for the Fitzmill;

(b) #12 and #20 mesh hand screens; and (c) #8 mesh screen for the oscillator.

Before beginning formulation of the tablets according to this example of the invention, all equipment should be checked to see that it is thoroughly cleaned and labeled to assist in the preparation of the tablets. Next, the weight of all ingredients should be verified.

To begin the process, the mixer speed should be set to about 40 RPM. Part I of the process is accomplished by passing the potassium salt of ibuprofen through the #3-P screen on the Fitzmill operating at high speed with impact hammers in the forward position. The ibuprofen salt then is put in the mixer.

Part II of the process involves preparation of a paste of starch and gelatin. First, the purified water specified in Part II is heated in a container to approximately 40 to 45 degree Centigrade. Using the mixer, the gelatin and starch specified in Part II are mixed slowly into the heated water until a clear slurry is formed. The mixture is heated until a paste is formed. Then the paste is blended in the mixer with the material resulting from Part I for approximately 15 minutes. Extra water may be added to adjust the wetness of the granulation to be formed. Continued mixing should be done for about 5 minutes. The wet granulation is formed by putting the wet mass that has just been mixed as described above through the #4-P screen on the Fitzmill operating at slow speed with impact hammers forward. Then approximately 10 kg. of the wet granulation is spread on each of a number of suitably sized trays, which are then placed in an approximately 55 degree Centigrade oven to dry the granulations. After drying, the size of the granulations may be reduced by passing the dried material through the #10 mesh screen in the oscillator. Then the mixer is cleaned and its speed is set to about 25 RPM. The reduced in size dried granules are then put in the mixer.

Next, the lactose and corn starch specified in Part III are passed through the #12 mesh hand screen into the mixer. The explotab and the cabosil are then mixed well in an appropriate container. This mixture is then passed through the #12 mesh screen into the mixer. The mixer is then allowed to blend the resulting mixture for about 7 minutes.

The magnesium stearate of Part IV is then passed through the #20 mesh screen into the mixer and the blending is continued for another predetermined time, for example, 3 minutes. The resulting bulk weight of the mixture should be approximately 60.0 kg.

The mixture is then compressed into tablets. The machines and equipment that may be used are as follows:

1. Tablet press such as a Stokes tablet press; and
2. Punches as follows:
   (a) 16 ¼" Standard upper punches;
   (b) 16 ¼" Standard lower punches; and
   (c) 16 ¼" Standard dies.

The procedure for compressing the mixture prepared in accordance with the steps described above is as follows. First, it should be insured that all machines and tools are clean and all containers, machines, and equipment used to make the tablets are properly labeled. Then the granulation prepared above is compressed into tablets by using the equipment specified above in the generally known manner in which this equipment is used to make tablets. The goal here is to make tablets which weigh approximately 600 mg. each. Ten tablets should weigh approximately 6.0 grams, with an allowed range of approximately 5.00 to 6.12 grams. The hardness of the resulting tablets may be checked with a Key hardness tester and the thickness of 10 tablets may be checked with a Monsanto Tablet Thickness Tester The friability of the tablets may be checked with a Friabilator.

The tablets then may be coated with a clear coating solution The ingredients needed to make such a solution may be as follows

| Ingredient | Quantity |
| --- | --- |
| Part I - Methocel Clear Coating Solution | |
| Hydroxypropyl Methylcellulose 2910 USP (Methocel E-15 Premium) (Film Base) | 2 kg. |
| Methylene Chloride FCC (15 L) (Solvent) | 28 kg. |
| Methyl Alcohol NF (21 L) (Solvent) | 12 kg. |
| Propylene Glycol USP (Film Base) | 700 ml. |
| Polyethylene Glycol 3350 NF (Film Base) | 150 g. |
| Castor Oil USP (Film Base) | 150 ml. |
| Part II - Methocel Clear Coating Solution | |
| From the results of Part I | 22 kg. |
| Opaspray (Premixed Film Coating) | 1 kg. |
| Part IIA - Methocel Clear Coating Solution | |
| Clear Opacoat NA-7013 (Film Coating) | 150 ml. |
| Methyl Alcohol NF (Solvent) | 225 ml. |
| Part III - Methocel Clear Coating Solution | |
| From the results of Part I | 22 kg. |
| Opaspray (Premixed Film Coating) | 1 kg. |
| Part IIIA - Methocel Clear Coating Solution | |
| Clear Opacoat NA-7013 (Film Coating) | 150 ml. |
| Methyl Alcohol NF (Solvent) | 225 ml. |

The procedure for preparing a clear Methocel coating solution is as follows. First, the methylene chloride of Part I is weighed into a clean, appropriate container. Then the methyl alcohol is weighed into the container. After that, the propylene glycol, castor oil, polyethylene glycol 3350, and Methocel specified in Part I are added to the container until dissolved by mixing the contents of the container. The resulting solution is then checked to make sure that the solution is clear and free from lumps. Mixing is continued until this is the case. The resulting solution is then separated into two equal parts, approximately 22 kg. each. The opaspray of Part II is passed through a #100 mesh screen and mixed with one of the equal parts of solution. The opaspray of Part III is passed through a #100 mesh screen and mixed with the other of the equal parts of solution.

A clear coating solution is then prepared by mixing the opacoat of Part IIA with the methyl alcohol of that Part in a clean appropriate container. The mixture is heated at an elevated temperature, such as about 37 degrees Centigrade, until a clear solution results.

Then it is advisable to check to see that all ducts and exhausts in the equipment to be used in the process described below is well cleaned. The bulk weight of the tablets may also be checked again.

The tablets are placed in a coating machine such as a Pellegrini coating machine and warmed for at least 15 minutes by jogging. Dust is removed by blowing air over the tablets with the exhaust slot wide open. Airless spray equipment then is used to cover the tablets with a film coating of the clear solution. The following parameters may be maintained: (a) pump pressure of about 30–40 PSI, (b) triggering air pressure of about 80–90 PSI, (c) distance between gun and tablets of about one foot, and (d) use of an appropriate nozzle such as tip number 1180 in the Pellegrini equipment. The tablets are first coated with the film coating and then with the clear solution.

After the coating is completed, the tablets are left in their pan and the pan speed is set at about 4 RPM. Warm air, which may have a temperature such that a temperature of about 37 degrees Centigrade is maintained on the tablet bed, is passed over the tablets to dry the tablets. This drying may be maintained for about 30 minutes. After the tablets are dried, they may be put in standard packaging drums.

EXAMPLE 2

A particularly advantageous solid dose tablet composition containing 200 mg. of the potassium salt of ibuprofen per tablet may be prepared as follows with the ingredients listed below:

| Ingredient | Quantity |
| --- | --- |
| Part I | |
| Potassium Ibuprofen Salt (Active Ingredient) | 20.0 kg. |
| Part II | |
| Starch NF (Corn Starch) (Binder) | 1.0 kg. |
| Gelatin USP (Binder) | 500 g. |
| Purified Water USP (Solvent) | 6.0 L. |
| Part III | |
| Lactose USP Spray Process (Filler, Binder) | 4.5 kg. |
| Starch NF (Corn Starch) (Binder) | 2.9 kg. |
| Sodium Starch Glycolate NF (Explotab) (Binder) | 750 g. |
| Cabosil M-5 Powder (Colloidal Silicon Dioxide NF) (Lubricant) | 150 g. |
| Part IV | |
| Magnesium Stearate NF Imp. Powder (Lubricant) | 200 g. |

The following dry granulation equipment may be used in this process:
1. A Marion Mixer G-5;
2. A Fitzmill;
3. A Drying Oven;
4. An Oscillator; and
5. A Number of Screens Comprising:
    (a) #3-P and #4-P mesh screens for the Fitzmill;
    (b) #12 and #20 mesh hand screens; and
    (c) #8 mesh screen for the oscillator.

Before beginning formulation of the tablets according to this example of the invention, all equipment should be checked to see that it is thoroughly cleaned and labeled to assist in the preparation of the tablets. Next, the weight of all ingredients should be verified.

To begin the process, the mixer speed should be set to about 40 RPM. Part I of the process is accomplished by passing the potassium salt of ibuprofen through the #3-P screen on the Fitzmill operating at high speed with impact hammers in the forward position. The ibuprofen salt then is put in the mixer.

Part II of the process involves preparation of a paste of starch and gelatin. First, the purified water specified in Part II is heated in a container to approximately 40 to 45 degree Centigrade. Using the mixer, the gelatin and starch specified in Part II are mixed slowly into the heated water until a clear slurry is formed. The mixture is heated until a paste is formed. Then the paste is blended in the mixer with the material resulting from Part I for approximately 15 minutes. Extra water may be added to adjust the wetness of the granulation to be formed. Continued mixing should be done for about 5 minutes. The wet granulation is formed by putting the wet mass that has just been mixed as described above through the #4-P screen on the Fitzmill operating at slow speed with impact hammers forward. Then approximately 10 kg. of the wet granulation is spread on each of a number of suitably sized trays, which are then placed in an approximately 55 degree Centigrade oven to dry the granules. After drying, the size of the granulations may be reduced by passing the dried material through the #10 mesh screen in the oscillator. Then the mixer is cleaned and its speed is set to about 25 RPM. The reduced in size dried granules are then put in the mixer.

Next, the lactose and corn starch specified in Part III are passed through the #12 mesh hand screen into the mixer. The explotab and the cabosil are then mixed well in an appropriate container. This mixture is then passed through the #12 mesh screen into the mixer. The mixer is then allowed to blend the resulting mixture for about 7 minutes.

The magnesium stearate of Part IV is then passed through the #20 mesh screen into the mixer and the blending is continued for another predetermined time, for example, 3 minutes. The resulting bulk weight of the mixture should be approximately 40.0 kg.

The mixture is then compressed into tablets. The machines and equipment that may be used are as follows:
1. Tablet press such as a Stokes tablet press; and
2. Punches as follows:
    (a) 16 ⅜" Standard upper punches;
    (b) 16 ⅜" Standard lower punches; and
    (c) 16 ⅜" Standard dies.

The procedure for compressing the mixture prepared in accordance with the steps described above is as follows. First, it should be insured that all machines and tools are clean and all containers, machines, and equipment used to make the tablets are properly labeled. Then the granulation prepared above is compressed into tablets by using the equipment specified above in the generally known manner in which this equipment is used to make tablets. The goal here is to make tablets which weigh approximately 400 mg. each. Ten tablets should weigh approximately 4.0 grams, with an allowed range of approximately 3.00 to 4.12 grams. The hardness of the resulting tablets may be checked with a Key hardness tester and the thickness of 10 tablets may be checked with a Monsanto Tablet Thickness Tester. The friability of the tablets may be checked with a Friabilator.

The tablets then may be coated with a clear coating solution. The ingredients needed to make such a solution may be as follows:

| Ingredient | Quantity |
| --- | --- |
| Part I - Methocel Clear Coating Solution | |
| Hydroxypropyl Methylcellulose 2910 USP (Methocel E-15 Premium) (Film Base) | 2 kg. |
| Methylene Chloride FCC (21 L) (Solvent) | 28 kg. |
| Methyl Alcohol NF (15 L) (Solvent) | 12 kg. |
| Propylene Glycol USP (Film Base) | 700 ml. |
| Polyethylene Glycol 3350 NF (Film Base) | 150 g. |
| Castor Oil USP (Film Base) | 150 ml. |
| Part II - Methocel Clear Coating Solution | |
| From the results of Part I | 22 kg. |
| Opaspray (Premixed Film Coating) | 1 kg. |
| Part IIA - Methocel Clear Coating Solution | |
| Clear Opacoat NA-7013 (Film Coating) | 150 ml. |
| Methyl Alcohol NF (Solvent) | 225 ml. |

-continued

| Ingredient | Quantity |
| --- | --- |
| Part III - Methocel Clear Coating Solution | |
| From the results of Part I | 22 kg. |
| Opaspray (Premixed Film Coating) | 1 kg. |
| Part IIIA - Methocel Clear Coating Solution | |
| Clear Opacoat NA-7013 (Film Coating) | 150 ml. |
| Methyl Alcohol NF (Solvent) | 225 ml. |

The procedure for preparing a clear Methocel coating solution is as follows. First, the methylene chloride of Part I is weighed into a clean, appropriate container. Then the methyl alcohol is weighed into the container. After that, the propylene glycol, castor oil, polyethylene glycol 3350, and Methocel specified in Part I are added to the container until dissolved by mixing the contents of the container. The resulting solution is then checked to make sure that the solution is clear and free from lumps. Mixing is continued until this is the case. The resulting solution is then separated into two equal parts, approximately 22 kg. each. The opaspray of Part II is passed through a #100 mesh screen and mixed with one of the equal parts of solution. The opaspray of Part III is passed through a #100 mesh screen and mixed with the other of the equal parts of solution.

A clear coating solution is then prepared by mixing the opacoat of Part IIA with the methyl alcohol of that Part in a clean appropriate container. The mixture is heated at an elevated temperature, such as about 37 degrees Centigrade, until a clear solution results.

Then it is advisable to check to see that all ducts and exhausts in the equipment to be used in the process described below is well cleaned. The bulk weight of the tablets may be also checked again.

The tablets are placed in Pellegrini and warmed for at least 15 minutes by jogging. Dust is removed by blowing air over the tablets with the exhaust slot wide open. Airless spray equipment then is used to cover the tablets with a film coating of the clear solution. The following parameters may be maintained: (a) pump pressure of about 30-40 PSI, (b) triggering air pressure of about 80-90 PSI, (c) distance between gun and tablets of about one foot, and (d) use of an appropriate nozzle such as the tip number 1180 in the Pellegrini equipment. The tablets are first coated with the film coating and then with the clear solution.

After the coating is completed, the tablets are left in their pan and the pan speed is set at about 4 RPM. Warm air, which may have a temperature such that a temperature of about 37 degrees Centigrade is maintained on the tablet bed, is passed over the tablets to dry the tablets. This drying may be maintained for about 30 minutes. After the tablets are dried, they may be put in standard packaging drums.

EXAMPLE 3

A 250 liter batch of a liquid ibuprofen composition in accordance with the invention of this application may be prepared as follows. The resulting composition will contain about 200 mg. of ibuprofen salt per 5 ml. of the liquid composition (about a teaspoonful sample of the composition). A list of the ingredients needed for the preparation of this batch is as follows:

| Ingredient | Quantity |
| --- | --- |
| Purified water USP Deionized | 100,000 ml. |
| Sodium carboxymethylcellulose 7 MF | 750 gm. |
| Sucrose NF XV (Holly) | 150,000 gm. |
| Potassium Ibuprofen Salt milled (60 mesh) | 10,000 gm. |
| Glycerin USP XXI (96%) | 20,000 ml. |
| Methyl paraben USP XIX | 200 gm. |
| Propyl paraben USP XIX | 100 gm. |
| Flavor | 1000 ml. |
| Water USP Deionized | qs. |
| Dicelite Speedex filter aid | 300 gm. |

Before preparing the composition, the preparation area should be checked for cleanliness, including all equipment coming in contact with the ingredients. In addition to the raw materials listed above, the following equipment should be available:
1. Fitzmill;
2. 80 gallon jacketed tank;
3. 100 gallon tank;
4. Transfer pump and Hoses; and
5. Filtration system To avoid microbial contamination, contact of the ingredients and the equipment with the hands should be avoided.

The purified water is placed in the 80 gallon tank which has been fitted with a double impeller stirrer. The stirrer has an impeller toward the bottom of the tank and an impeller toward the top of the tank so that adequate mixing is obtained from top to bottom in the tank. The water in the tank is then heated to a temperature of about 55 to 65 degrees Centigrade.

The 750 grams of sodium carboxymethylcellulose powder then are slowly added to the heated water while it is being stirred at high speed. Once this powder has dissolved completely, then the 150,000 gm. of sucrose are slowly added to the solution while it is stirred at high speed. (Although it is not mentioned in the list of ingredients above, an artificial sweetener such as sodium saccharine may be added to further enhance the sweetness of the resulting composition.) When the sucrose has been dissolved, the solution is permitted to cool until it has a temperature of about 20 to 30 degrees Centigrade.

The milled ibuprofen salt is slowly added to the tank while the contents of the tank is being stirred. Glycerin then may be added to the tank which undergoes continued stirring. The tank then is allowed to stand until any froth that may have appeared has subsided. If the froth does not subside, the mixture should be stirred again and allowed to stand until it becomes clear.

The parabens and a flavoring such as banana or cherry flavoring then are added to the main processing tank while its contents are being stirred at high speed. More deionized water is then added to the tank so that the contents of the tank is 250 liters of liquid ibuprofen composition. A calibrated dip stick may be used to measure the amount of liquid in the tank. When 250 liters of liquid are in the tank, it is mixed thoroughly for about ten minutes.

A filtration system such as a Sparkler filter Model 18-S-7 is then set up according to manufacturer's instructions using filter paper having one layer of 17 micron cotton rag underlined by a 40 micron lint free rayon cellulose binder. Dicelite Speedx filter aid is added to the batch which is then mixed for ten minutes. The batch then is filtered into a clean 100 gallon stainless steel tank, which then may be sealed to prevent loss of volatiles.

A clear, stable, and palatable liquid ibuprofen composition having about 200 mg. of ibuprofen salt per 5 ml. sample results at this time. The pH of the composition is between about 7.0 and about 8.0 and it has none of the unpleasant taste and much less of the burning sensation produced by prior liquid ibuprofen compositions. It is believed that compositions having pH's close to neutral in the manner of this composition are instrumental in reducing the gastrointestinal distress because neutral pH compositions are believed to not influence or in any way upset the natural pH balance of the gastrointestinal tract when they are administered as was the case when prior acidic compositions such as aspirin or ibuprofen were administered.

EXAMPLE 4

A 250 liter batch of a liquid ibuprofen composition containing about 25 mg. of ibuprofen salt per 5 ml. of the composition may be prepared in accordance with the steps of Example 3 with the exception that 1 250 grams of ibuprofen salt are used instead of the 20,000 grams of ibuprofen salt specified in Example 3. Using 2,500 grams of ibuprofen salt in this Example instead of 1,250 grams will result in a liquid composition having about 50 mg. of ibuprofen salt per 5 ml.

EXAMPLE 5

A 250 liter batch of a liquid ibuprofen composition containing about 100 grams of ibuprofen salt per 5 ml. may be prepared in accordance with the steps of Example 3 with the exception that 5,000 grams of ibuprofen salt is used instead of the 20,000 grams of ibuprofen salt specified in Example 3. Using 10,000 grams of ibuprofen salt in this Example instead of 5,000 grams will result in a liquid composition having about 200 mg. of ibuprofen salt per 5 ml.

EXAMPLE 6

A 250 liter batch of a liquid ibuprofen composition containing about 400 mg. of ibuprofen salt per 5 ml. sample of the composition may be prepared in accordance with the steps of Example 3 with the exception that no ethyl alcohol is used. The methyl paraben, propyl paraben, and menthol are added to water heated to 55 to 65 degrees Centigrade and dissolved in the heated water and then cooled before being added to the batch. 250 liter batches of liquid ibuprofen salt composition containing about 25 mg., 50 mg., 100 mg., and 200 mg. of ibuprofen per 5 ml. sample of the composition may be prepared in accordance with Examples 4 and 5, as modified by the exception to the steps of Example 3 specified in this Example.

EXAMPLE 7

A 250 liter batch of a liquid ibuprofen composition containing about 400 mg. of ibuprofen salt per 5 ml. sample of the composition may be prepared in accordance with the steps of Example 3 with the exception that no ethyl alcohol or menthol is used. The methyl paraben and propyl paraben are added to heated water as above and cooled and then added to the batch. 250 liter batches of liquid ibuprofen composition containing about 25 mg., 50 mg., 100 mg., and 200 mg. of ibuprofen salt per 5 ml. sample of the composition may be prepared in accordance with Examples 4 and 5, as modified by the exception to the steps of Example 3 specified in this Example.

EXAMPLE 8

A 250 liter batch of a liquid ibuprofen composition in accordance with the invention of this application may be prepared as follows. The resulting composition will contain about 400 mg. of ibuprofen salt per 5 ml. of the liquid composition (about a teaspoonful sample of the composition). A list of the ingredients needed for the preparation of this batch is as follows:

| Ingredient | Quantity |
| --- | --- |
| Ibuprofen milled (60 mesh) | 20,000 gm. |
| Sodium carboxymethylcellulose 7 MF | 750 gm. |
| Sucrose NF XVI | 125,000 gm. |
| Potassium bicarbonate USP XXI powder | 11,500 gm. |
| Glycerin USP XXI (96%) | 12,500 ml. |
| Ethyl alcohol 190 proof USP XXI | 40,400 ml. |
| Methyl paraben USP XVI | 200 gm. |
| Propyl paraben USP XVI | 100 gm. |
| Menthol USP XXI | 100 gm. |
| Flavor | 1000 ml. |
| Purified water USP XXI | 100,000 ml. |
| Dicelite Speedex filter aid | 300 gm. |

Before preparing the composition, the preparation area should be checked for cleanliness, including all equipment coming in contact with the ingredients. In addition to the raw materials listed above, the following equipment should be available:
 1. Fitzmill;
 2. 80 gallon jacketed tank;
 3. 100 gallon tank;
 4. Transfer pump and hoses; and
 5. Filtration system To avoid microbial contamination, contact of the ingredients and the equipment with the hands should be avoided.

The purified water is placed in the 80 gallon tank which has been fitted with a double impeller stirrer. The stirrer has an impeller toward the bottom of the tank and an impeller toward the top of the tank so that adequate mixing is obtained from top to bottom in the tank. The water in the tank is then heated to a temperature of about 55 to 65 degrees Centigrade.

The 750 grams of sodium carboxymethylcellulose powder then are slowly added to the heated water while it is being stirred at high speed. Once this powder has dissolved completely, then the 125,000 gm. of sucrose are slowly added to the solution while it is stirred at high speed. When the sucrose has been dissolved, the solution is permitted to cool until it has a temperature of about 20 to 30 degrees Centigrade.

Using a Fitzmill with a screen and its hammers forward, 11,500 grams of potassium bicarbonate powder are milled into a tared container. Then the potassium bicarbonate powder is added to the processing tank while the contents of the tank continues to be stirred. After the potassium bicarbonate has been dissolved, then the milled ibuprofen is slowly added to the tank while the contents of the tank is being stirred. Glycerin then may be added to the tank which undergoes continued stirring. The tank then is allowed to stand until the froth that has appeared has subsided. If the froth does not subside, the mixture should be stirred again and allowed to stand until it becomes clear.

Next, the ethyl alcohol is placed in a suitable stainless steel vessel. The methyl paraben, propyl paraben, and menthol are then dissolved in the alcohol. Stirring is used to aid in dissolving these ingredients. Flavoring such as banana flavoring or cherry flavoring is added to the alcohol at this time. The alcoholic solution is then added to the main processing tank while its contents are being stirred at high speed. More deionized water is then added to the tank so that the contents of the tank is 250 liters of liquid ibuprofen composition. A calibrated dip stick may be used to measure the amount of liquid in the tank. When 250 liters of liquid are in the tank, it is mixed thoroughly for about ten minutes.

A filtration system such as a Sparkler filter Model 18-S-7 is then set up according to manufacturer's instructions using filter paper having one layer of 17 micron cotton rag underlined by a 40 micron lint free rayon cellulose binder. Dicelite Speedex filter aid is added to the batch which is then mixed for ten minutes. The batch then is filtered into a clean 100 gallon stainless steel tank, which then may be sealed to prevent loss of volatiles.

A clear, stable, and palatable liquid ibuprofen composition having about 400 mg. of ibuprofen salt per 5 ml. sample results at this time because of the fact that the ibuprofen is converted into an alkali metal salt of ibuprofen, in this case the potassium salt, through a reaction with an alkali metal bicarbonate.

EXAMPLE 9

A 250 liter batch of a liquid ibuprofen composition containing about 25 mg. of ibuprofen salt per 5 ml. of the composition may be prepared in accordance with the steps of Example 8 with the exception that 1,250 grams of ibuprofen is used instead of the 20,000 grams of ibuprofen specified in Example 8. Using 2,500 grams of ibuprofen in this Example instead of 1,250 grams will result in a liquid composition having about 50 mg. of ibuprofen salt per 5 ml.

EXAMPLE 10

A 250 liter batch of a liquid ibuprofen composition containing about 100 grams of ibuprofen salt per 5 ml. may be prepared in accordance with the steps of Example 8 with the exception that 5,000 grams of ibuprofen is used instead of the 20,000 grams of ibuprofen specified in Example 8. Using 10,000 grams of ibuprofen in this Example instead of 5,000 grams will result in a liquid composition having about 200 mg. of ibuprofen salt per 5 ml.

EXAMPLE 11

A 250 liter batch of a liquid ibuprofen composition containing about 400 mg. of ibuprofen salt per 5 ml. sample of the composition may be prepared in accordance with the steps of Example 8 with the exception that no ethyl alcohol is used. The methyl paraben and propyl paraben are added directly to the batch and the menthol is added to water heated to 55 to 65 degrees Centigrade and dissolved in the heated water before being added to the batch. 250 liter batches of liquid ibuprofen composition containing about 25 mg., 50 mg., 100 mg., and 200 mg. of ibuprofen salt per 5 ml. sample of the composition may be prepared in accordance with Examples 9 and 10, as modified by the exception to the steps of Example 8 specified in this Example.

EXAMPLE 12

A 250 liter batch of a liquid ibuprofen composition containing about 400 mg. of ibuprofen salt per 5 ml. sample of the composition may be prepared in accordance with the steps of Example 8 with the exception that no ethyl alcohol or menthol is used. The methyl paraben and propyl paraben are added directly to the batch. 250 liter batches of liquid ibuprofen composition containing about 25 mg., 50 mg., 100 mg., and 200 mg. of ibuprofen salt per 5 ml. sample of the composition may be prepared in accordance with Examples 9 and 10, as modified by the exception to the steps of Example 8 specified in this Example.

EXAMPLE 13

A aqueous film coating may be used in place of the Methocel film coating in the procedure for preparing tablets of Examples 1 and 2. The aqueous film coating comprises the following ingredients:

| Ingredients | Quantity |
| --- | --- |
| Part I | |
| Purified Water USP (Deionized) | 41.7 ml. |
| Hydroxypropyl Methylcellulose USP E-15 | 2.503 g. |
| Hydroxypropyl Methylcellulose USP E-5 | 2.503 g. |
| Part II | |
| Purified Water USP (Deionized) | 2.9 L. |
| Polyethylene Glycol 4000 NF USP | 1.015 kg. |
| Part III | |
| Opaspray (Colorcon) | 6.06 kg. |

The aqueous film coating solution is prepared as follows and is used in the manner the Methocel coating solution is used in Examples 2 and 3. First, the purified water of Part I is added to a suitable stainless steel container with a stirring device. Then the hydroxypropyl methylcelluloses are added to the container while the contents are being stirred. The contents of the container should not be over stirred because such over stirring will thin the coating solution.

Next, the purified water of Part II is added to a suitable stainless steel container with stirring device. The water is then heated to about 70 degrees Centigrade and the polyethylene glycol is added to the water while it is being stirred so as to dissolve the polyethylene glycol.

Then any color Opaspray (Colorcon) is stirred into the water solution of methylcelluloses until it is dispersed. The solution containing the Opaspray is then mixed with the solution containing polyethylene glycol.

EXAMPLE 14

Tablets containing 600 mg. of alkali metal ibuprofen salt per tablet and 800 mg. of alkali metal ibuprofen salt per tablet may be prepared in accordance with the procedures of Examples 1, 2, and 13. In the case of the 600 mg. per tablet composition, all that would have to be done is to combine the amounts of ingredients used in Examples 1 and 2 and to increase the size of the tablets to accommodate the increased amount of active ingredient. Similarly, for the 800 mg. per tablet composition, the amounts of Example 1 need to be doubled and the tablet size needs to be increased to accommodate the increased amount of active ingredient.

I claim:

1. A solid crystalline composition of matter, comprising:
an alkali metal salt of ibuprofen.

2. The composition of matter of claim 1, in which the alkali metal salt of ibuprofen is the potassium salt of ibuprofen.

3. The composition of matter of claim 1, in which the alkali metal salt of ibuprofen is the sodium salt of ibuprofen.

4. A solid dosage of ibuprofen, comprising:
a predetermined amount of an alkali metal salt of ibuprofen.

5. The solid dosage of ibuprofen of claim 4, in which the alkali metal salt of ibuprofen is the potassium salt of ibuprofen.

6. The solid dosage of ibuprofen of claim 4, in which the alkali metal salt of ibuprofen is the sodium salt of ibuprofen.

7. A process of preparing an alkali metal salt of ibuprofen, comprising the steps of:
dissolving a predetermined amount of an alkali metal bicarbonate in an aqueous medium; and
dissolving a predetermined amount of an ibuprofen composition in the aqueous medium.

8. The process of claim 7, further comprising the step of extracting solid alkali metal ibuprofen salt from the aqueous medium.

9. The process of claim 7, in which the alkali metal bicarbonate comprises potassium bicarbonate and the alkali metal salt of ibuprofen comprises the potassium salt of ibuprofen.

10. The process of claim 7, in which the alkali metal bicarbonate comprises sodium bicarbonate and the alkali metal salt of ibuprofen comprises the sodium salt of ibuprofen.

11. The process of claim 7, in which the step of dissolving a predetermined amount of an alkali metal bicarbonate in an aqueous medium comprises the step of dissolving a predetermined number of moles of alkali metal bicarbonate in the aqueous medium; and
in which the step of dissolving a predetermined amount of an ibuprofen composition in the aqueous medium comprises the step of dissolving a predetermined number of moles of ibuprofen composition in the aqueous medium;
the predetermined number of moles of alkali metal bicarbonate being at least as great as the predetermined number of moles of ibuprofen composition.

12. The process of claim 11, in which the predetermined number of moles of alkali metal bicarbonate is greater than the predetermined number of moles of ibuprofen composition to assist in the complete and efficient conversion of ibuprofen composition into the alkali metal salt of ibuprofen.

13. A process of rapidly and effectively alleviating pain in a mammal, comprising the step of:
administering an alkali metal salt of ibuprofen to the mammal.

14. The process of claim 13, in which the administering step comprises the step of administering a solid dose of the alkali metal salt of ibuprofen to the mammal.

15. The process of claim 13, in which the administering step comprises the step of administering a liquid dose of the alkali metal salt of ibuprofen to the mammal.

16. The process of claim 15, in which the administering step comprises the step of administering an aqueous solution of the alkali metal salt of ibuprofen to the mammal.

17. A process of rapidly and effectively reducing inflammation of tissues in a mammal, comprising the step of:
administering an alkali metal salt of ibuprofen to the mammal.

18. The process of claim 17, in which the administering step comprises the step of administering a solid dose of the alkali metal salt of ibuprofen to the mammal.

19. The process of claim 17, in which the administering step comprises the step of administering a liquid dose of the alkali metal salt of ibuprofen to the mammal.

20. The process of claim 19, in which the administering step comprises the step of administering an aqueous solution of the alkali metal salt of ibuprofen to the mammal.

21. A process of rapidly and effectively reducing fever in a mammal, comprising the step of:
administering an alkali metal salt of ibuprofen to the mammal.

22. The process of claim 21, in which the administering step comprises the step of administering a solid dose of the alkali metal salt of ibuprofen to the mammal.

23. The process of claim 21, in which the administering step comprises the step of administering a liquid dose of the alkali metal salt of ibuprofen to the mammal.

24. The process of claim 23, in which the administering step comprises the step of administering an aqueous solution of the alkali metal salt of ibuprofen to the mammal.

25. A liquid ibuprofen composition lacking the flavor of ibuprofen and having a reduced burning sensation when administered orally, comprising:
a predetermined amount of alkali metal bicarbonate composition dissolved in an aqueous medium;
a predetermined amount of ibuprofen composition dissolved in the aqueous medium;
in which the number of moles of alkali metal bicarbonate dissolved in the aqueous medium is at least as great as the number of moles of ibuprofen composition dissolved in the aqueous medium.

26. The liquid composition of claim 25, in which the ratio of the number of moles of alkali metal bicarbonate composition dissolved in the aqueous medium to the number of moles of ibuprofen composition dissolved in the aqueous medium being such that the flavor of ibuprofen is substantially eliminated and the burning sensation is substantially reduced when the liquid composition is administered orally.

* * * * *